(12) United States Patent
Espitalie et al.

(10) Patent No.: US 8,796,035 B2
(45) Date of Patent: Aug. 5, 2014

(54) METHOD AND DEVICE FOR FAST SULFUR CHARACTERIZATION AND QUANTIFICATION IN SEDIMENTARY ROCKS AND PETROLEUM PRODUCTS

(75) Inventors: Jean Espitalie, Le Vésinet (FR); Roland Antonas, Courbevoie (FR); Violaine Lamoureux-Var, Chatou (FR); Gérémie Letort, Limay (FR); Daniel Pillot, Chatou (FR); Valérie Beaumont, Montreuil-sous-Bois (FR); Frank Haeseler, La Garenne Colombes (FR)

(73) Assignees: IFP Energies Nouvelles, Rueil-Malmaison Cedex (FR); Vinci Technologies, Nanterre (FR)

( * ) Notice: Subject to any disclaimer, the term of this patent is extended or adjusted under 35 U.S.C. 154(b) by 635 days.

(21) Appl. No.: 13/126,851

(22) PCT Filed: Oct. 27, 2009

(86) PCT No.: PCT/FR2009/001253
§ 371 (c)(1),
(2), (4) Date: Jul. 15, 2011

(87) PCT Pub. No.: WO2010/049609
PCT Pub. Date: May 6, 2010

(65) Prior Publication Data
US 2011/0263034 A1   Oct. 27, 2011

(30) Foreign Application Priority Data
Oct. 29, 2008  (FR) .................................... 08 06015

(51) Int. Cl.
 *G01N 33/24* (2006.01)
 *G01N 31/12* (2006.01)
(52) U.S. Cl.
 USPC ................ 436/122; 422/78; 422/79; 422/80;
  436/31; 436/32; 436/119; 436/120; 436/121;
  436/123; 436/155; 436/157; 436/159; 436/160
(58) Field of Classification Search
 USPC .......... 422/78–80; 436/31–32, 119–123, 155,
  436/157, 159–160, 139
 See application file for complete search history.

(56) References Cited

U.S. PATENT DOCUMENTS 3,953,171 A * 4/1976 Espitalie et al. ................ 436/32
4,120,659 A * 10/1978 Cropper ......................... 436/123

(Continued)

FOREIGN PATENT DOCUMENTS

EP  0 767 375 A1  4/1997
FR  2 376 414      7/1978

(Continued)

OTHER PUBLICATIONS

Jensen, H. K. B. et al, Organic Geochemistry 1998, 28, 87-110.*

(Continued)

*Primary Examiner* — Arlen Soderquist
(74) *Attorney, Agent, or Firm* — Antonelli, Terry, Stout & Kraus, LLP.

(57) ABSTRACT

The invention relates to a method and to a device for sulfur characterization and quantification in a sample of sedimentary rocks or of petroleum products wherein the following stages are carried out: heating said sample in a pyrolysis oven (1) in a non-oxidizing atmosphere, oxidizing part of the pyrolysis effluents and continuously measuring the amount of $SO_2$ generated by said part after oxidation, then transferring the pyrolysis residue of said sample into an oxidation oven (1') and continuously measuring the amount of $SO_2$ contained in the effluents resulting from said oxidation heating.

20 Claims, 2 Drawing Sheets

(56) References Cited

U.S. PATENT DOCUMENTS

| | | | |
|---|---|---|---|
| 4,153,415 A * | 5/1979 | Espitalie et al. | 436/31 |
| 4,213,763 A * | 7/1980 | Madec et al. | 436/32 |
| 4,229,181 A * | 10/1980 | Espitalie et al. | 436/31 |
| 4,244,917 A * | 1/1981 | Woods et al. | 422/78 |
| 4,352,673 A * | 10/1982 | Espitalie et al. | 436/145 |
| 4,485,071 A * | 11/1984 | Larter | 422/78 |
| 4,519,983 A * | 5/1985 | Espitalie et al. | 422/78 |
| 4,578,356 A * | 3/1986 | Larter | 436/31 |
| 4,824,790 A * | 4/1989 | Carangelo et al. | 436/157 |
| 4,837,158 A * | 6/1989 | Toulhoat et al. | 436/37 |
| 4,845,040 A * | 7/1989 | Moon et al. | 436/120 |
| 5,204,270 A * | 4/1993 | LaCount | 436/157 |
| 5,330,714 A * | 7/1994 | Godec et al. | 422/52 |
| 5,786,225 A * | 7/1998 | Lafargue et al. | 436/147 |
| 5,811,308 A * | 9/1998 | Espitalie et al. | 436/145 |
| 5,843,787 A * | 12/1998 | Trabelsi et al. | 436/139 |
| 5,958,777 A * | 9/1999 | Espitalie et al. | 436/32 |
| 6,048,497 A * | 4/2000 | Lafargue et al. | 422/80 |
| 6,254,828 B1 * | 7/2001 | LaCount | 422/78 |
| 7,772,004 B2 * | 8/2010 | Lorant | 436/32 |
| 2003/0049854 A1 * | 3/2003 | Rhodes | 436/106 |
| 2005/0129578 A1 * | 6/2005 | Olstowski | 422/78 |
| 2008/0026471 A1 * | 1/2008 | Lorant | 436/32 |
| 2010/0120162 A1 * | 5/2010 | Stich | 436/119 |

FOREIGN PATENT DOCUMENTS

| | | |
|---|---|---|
| GB | 1 461 518 | 1/1977 |
| WO | WO 2005/111603 A1 | 11/2005 |

OTHER PUBLICATIONS

Behar, F. et al, Oil & Gas Science and Technology 2001, 56, 111-134.*

* cited by examiner

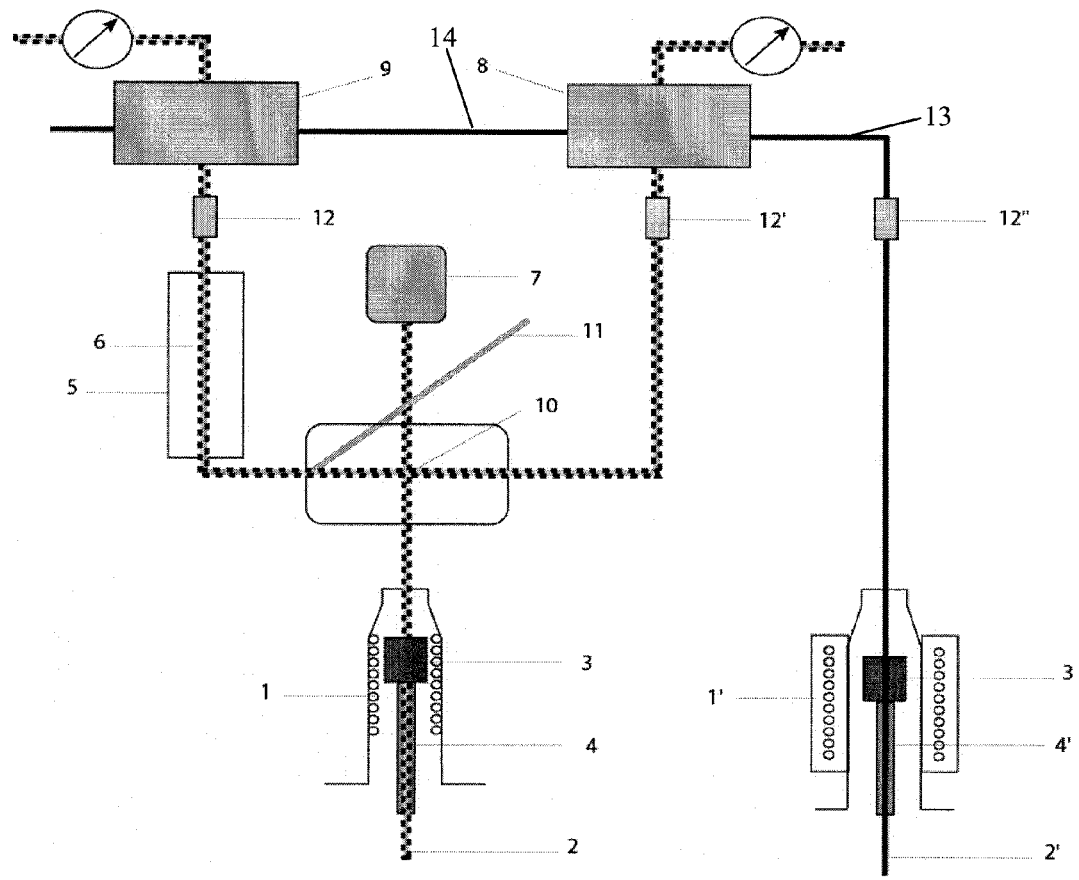
Figure 1
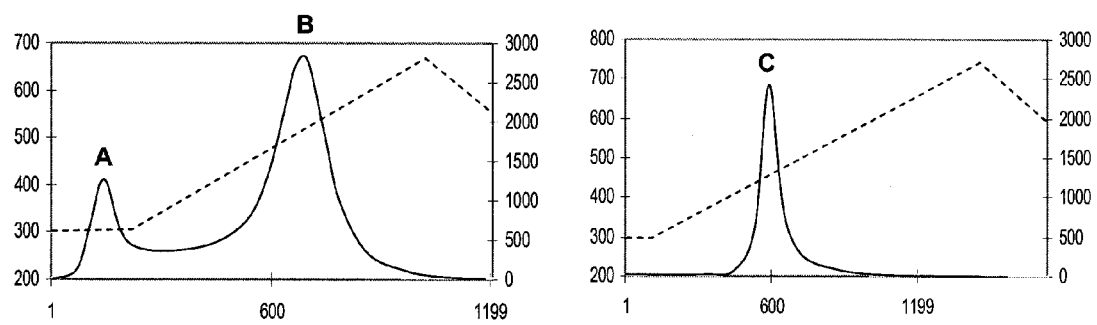
Figure 2-a
Figure 2-b

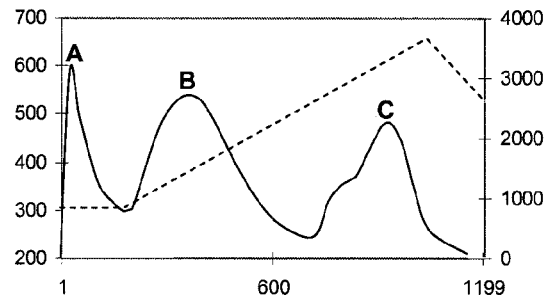
Figure 3-a
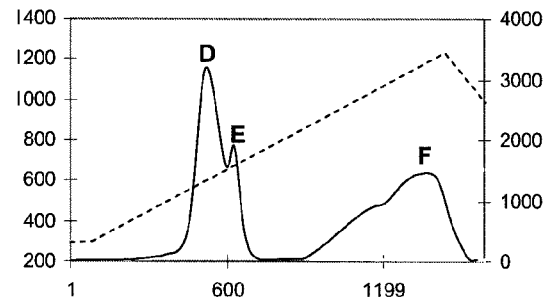
Figure 3-b
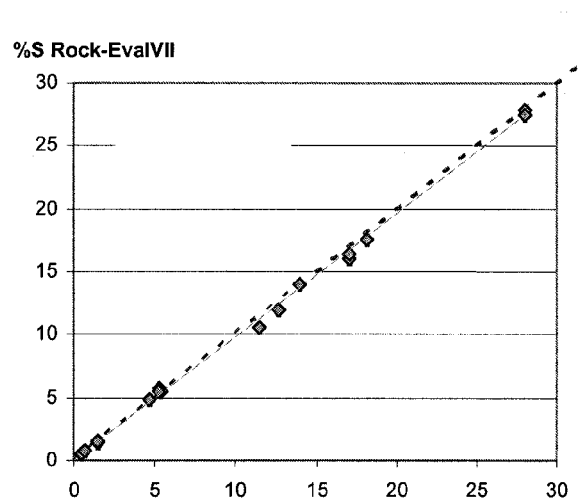
Figure 4

METHOD AND DEVICE FOR FAST SULFUR CHARACTERIZATION AND QUANTIFICATION IN SEDIMENTARY ROCKS AND PETROLEUM PRODUCTS

FIELD OF THE INVENTION

The sphere of application of this invention relates to a method and to a device for carrying out sulfur quantification measurements on samples of sediments, petroleum products or other materials. In particular, it allows to characterize and to quantify the sulfur in sedimentary rocks and in petroleum products (crudes, petroleum fractions, refining products, etc.), simultaneously with hydrocarbon and carbon quantification. The analysis time under standard conditions can be of the order of ninety minutes.

The petroleum industry increasingly turns to the production of unconventional crude oils that are richer in sulfur than conventional oils. Besides, the sulfur content constraints for refinery products are becoming more and more drastic.

For these reasons, it is essential to be able to quantify the sulfur in petroleum products and in the rocks of geological petroleum systems, and to characterize it as finely as possible.

Now, such fine measurements are delicate or even impossible in some cases.

For example, it is impossible to define the various molecular forms of organic sulfur in organic compounds containing more than 40 carbon atoms, which however are the petroleum compounds with the highest sulfur content. On the other hand, discriminating the organic sulfur from the mineral sulfur in a rock requires several operations with the currently known means.

The present invention allows to provide information on the sulfur types, even in a very heavy oil, and it allows to discriminate the organic sulfur from the mineral sulfur in a rock. The main goal thereof is to be applied in the following spheres:

Petroleum Exploration:
to help characterize the type of organic matter,
to identify the quality of the oil in terms of sulfur,
to seek a correlation between the petroleum and the mother rock,
to indicate a level of biodegradation, a phenomenon that causes sulfur concentration.

Petroleum Production:
to assess the $H_2S$ production risk according to the type of sulfur in presence, within the context of enhanced recovery with thermal processes.

Refining:
within the context of oil desulfurization.

SUMMARY OF THE INVENTION

The present invention thus relates to a method for sulfur characterization and quantification in a sample of sedimentary rocks or of petroleum products, wherein the following stages are carried out:

heating said sample in a pyrolysis oven in a non-oxidizing atmosphere, transferring the pyrolysis residues of said sample into an oxidation oven and continuously measuring the amount of $SO_2$ contained in the effluents resulting from said oxidation heating, oxidizing part of the pyrolysis effluents and continuously measuring the amount of $SO_2$ contained in said part after oxidation, According to a variant of the method, it is possible to measure:
the amounts of hydrocarbon-containing products, of CO and of $CO_2$ contained in the pyrolysis effluents,
the amounts of CO and of $CO_2$ contained in the effluents resulting from said oxidation heating.

The temperature of the pyrolysis oven can range between 60° C. and 800° C.

The temperature of the oxidation oven can range between 100° C. and 1300° C.

Said part of the pyrolysis effluents can be oxidized in an oven comprising a catalyst.

The invention also relates to a device for sulfur characterization and quantification on a sample of sedimentary rocks or of petroleum products, comprising:

a pyrolysis oven for heating said sample in a non-oxidizing atmosphere, means for transferring the pyrolysis residues of said sample into an oxidation oven, means for continuous measurement of the amount of $SO_2$ contained in the effluents resulting from said oxidation heating, means for oxidizing part of the pyrolysis effluents, means for continuous measurement of the amount of $SO_2$ contained in said part after oxidation.

The device can comprise three-way distribution means for the pyrolysis effluents.

The distribution means can be heated to a temperature ranging between 400° C. and 600° C.

One of the ways can carry the pyrolysis effluent to said oxidation means so as to oxidize the sulfur compounds to $SO_2$.

The means for oxidizing part of the pyrolysis effluents can comprise an oven, a catalyst and an air supply means.

One of the ways can carry the pyrolysis effluent to CO and $CO_2$ measuring means.

One of the ways can carry the pyrolysis effluent to hydrocarbon compound measuring means.

The method according to the invention is thus based on the measurement of the sulfur-containing gases emitted by a sample subjected to pyrolysis, then to oxidation.

1. Pyrolysis Stage:

The sample is pyrolyzed according to a predetermined temperature programme, in an oven swept by a non-oxidizing gas stream. Part of the pyrolysis effluents is carried along to a flame ionization detector where the hydrocarbons are quantified. Another part is carried along to a $CO_2$ and CO detector. A third part is oxidized in an oxidation oven, in the presence of air and optionally of a catalyst, where the sulfur-containing gases are oxidized to $SO_2$. This $SO_2$ is then continuously measured, by means of a UV or IR spectrophotometer for example. An $SO_2$ measurement as a function of the pyrolysis temperature and of time is thus obtained.

2. Oxidation Stage (Hot Oxidation):

The sample that has undergone the pyrolysis stage is transferred from the pyrolysis oven to an oxidation oven where the residue is oxidized according to a predetermined temperature programme, in an air stream. The oxidation effluents are carried along to $SO_2$, CO and $CO_2$ detection means for continuous measurement of these gases. An $SO_2$ measurement as a function of the oxidation temperature and of time is thus obtained.

Sulfur Characterization:

The results of these thermal treatments are two $SO_2$ profiles, the first one as a function of the pyrolysis temperature and the second as a function of the oxidation temperature. Each $SO_2$ profile comprises various peaks and it can be identified by the number of these peaks, their peak top temperature, their shape and their area. The two profiles thus make up a unique footprint characterizing the sulfur of the sample. This footprint notably allows to discriminate various types of sulfur compounds, such as a "labile" organic sulfur, a "very labile" organic sulfur, a "refractory" organic sulfur and the sulfur from pyrite $FeS_2$.

Sulfur Content Quantification:

The ratio of the $SO_2$ peak area to the area of a reference sample whose sulfur content is known allows to deduce the sulfur content of the sample analyzed. The proportion of so-called pyrolysis sulfur it contains, released during pyrolysis, and the proportion of so-called oxidation sulfur it contains, released during oxidation of the pyrolysis residue, are thus experimentally quantified. The sum of these two proportions is equal to the total sulfur content.

The present invention affords the following advantages:

Various Sample Types:

This method allows to study a wide range of sample types, such as:
  mother rocks,
  kerogens,
  coals,
  reservoir rocks,
  crude oils,
  petroleum fractions such as asphaltenes,
  petroleum distillates,
  it is in particular well suited for heavy organic products.

Small Sample Amount:

Analysis requires only some milligrams for liquids and several ten milligrams for rocks.

Short Analysis Time:

It can last from sixty to ninety minutes according to the sample analyzed.

Ease of Use of the Device:

Once the sample fed into the device, the automaton carries out all the stages.

Novel Information on the Sulfur Type:

Besides the fact that it quantifies the total sulfur content, the method allows to discriminate different sulfur types, which is difficult and long using other techniques (two-dimensional gas chromatography, X-ray absorption near edge structure (XANES) spectroscopy, etc.), or even impossible depending on the sulfur type:
  "very labile" organic sulfur
  "labile" organic sulfur
  non-pyrolysable sulfur referred to as "refractory" sulfur
  pyritic sulfur
  sulfates
  Obtaining a unique sulfur footprint for each sample.

BRIEF DESCRIPTION OF THE FIGURES

Other features and advantages of the present invention will be clear from reading the description hereafter of an embodiment and of examples given by way of non limitative example, with reference to the accompanying figures wherein:

FIG. 1 diagrammatically illustrates the device according to the invention,

FIG. 2a shows, in the case of a crude oil, an example of a record of the $SO_2$ released during pyrolysis, FIG. 2b shows, in the case of a crude oil, an example of a record of the $SO_2$ released during oxidation, FIG. 3a shows, in the case of a mother rock, an example of a record of the $SO_2$ released during pyrolysis, FIG. 3b shows, in the case of a mother rock, an example of a record of the $SO_2$ released during oxidation, FIG. 4 shows the total sulfur contents of different types of samples, oils, heavy oils, kerogens, pure sulfur compounds, measured with this invention (ordinate) and by coulometry (abscissa).

DETAILED DESCRIPTION

The device for implementing the method mainly consists of three ovens and three detectors.

Two ovens are used for thermal treatment of the sample: one, swept by an inert gas stream, is intended for pyrolysis of the sample, and the other, swept by an air or oxygen stream, is intended for oxidation of the pyrolysis residue.

A third oven is dedicated to oxidation of a fraction of the pyrolysis effluents. The three detectors are: a flame ionization detector (FID) for the hydrocarbons from the pyrolysis, an infrared (IR) spectrophotometer for the CO and the $CO_2$ from the pyrolysis and the oxidation, and an ultraviolet (UV) or infrared (IR) spectrophotometer for the $SO_2$ from the pyrolysis and the oxidation.

FIG. 1 illustrates an embodiment of the device according to the invention. A pyrolysis oven 1 heats the sample to between 60° C. and 800° C., with a predetermined temperature programme. The heating rate ranges between 1° C./min and 50° C./min. The oven is swept by an inert gas, nitrogen for example, with a flow rate ranging between 50 ml/min and 200 ml/min, which carries the pyrolysis effluents along to the analyzers. The nitrogen is fed into the oven through a pipe 2. Boat 3 contains the sample. The oven can be made of stainless steel, alumina, china, quartz or any other suitable material. Boat 3 can be made of stainless steel. However, in the case of sulfur analysis and for high-temperature oxidations, the boat is preferably made of alumina or china, so as to prevent sulfur retention on the walls thereof and so that it withstands high temperatures. This boat is fed into the pyrolysis oven by means of a piston 4. The piston can be made of stainless steel, but it is preferably made of alumina or china so as to withstand oxidation at high temperatures.

An oxidation oven 1' heats the pyrolysis residue to between 100° C. and 1300° C., with a predetermined temperature programme. The oven is swept by air or oxygen with a constant flow rate ranging between 50 ml/min and 200 ml/min. This carrier gas is fed into the oven through pipe 2' and it carries the oxidation effluents along to the analyzers. Boat 3 contains the sample after pyrolysis. It is fed into the oxidation oven by means of a piston 4'.

A pyrolysis effluent oxidation oven 5 is arranged between the pyrolysis oven and the $SO_2$ analyzer. It is intended to convert the sulfur-containing pyrolysis effluents to $SO_2$. Oxidation takes place at a constant temperature ranging between 500° C. and 1000° C., in the presence of air or oxygen. This oven can work, according to its temperature, with an oxidation catalyst 6, tungsten trioxide ($WO_2$) for example, or without a catalyst.

A gas stream divider 10, heated to between 400° C. and 600° C., is arranged at the outlet of pyrolysis oven 1. It is associated with two pumps and two mass flow rate meters, and it allows the gas stream flowing out of pyrolysis oven 1 to be divided three ways:
  one oriented toward FID detector 7,
  a second one oriented toward infrared spectrometer 8,
  a third one oriented toward infrared or ultraviolet spectrometer 9, after passage through oxidation oven 5.

A pipe 11 arranged between stream divider 10 and pyrolysis effluent oxidation oven 5 allows delivery of the air or of the oxygen that will serve for oxidation of the pyrolysis effluents.

An electronic flow rate regulation system associated with two pumps allows the flow rates of the gas streams sent to the detectors to be controlled.

Flame ionization detector 7 (FID) measures the hydrocarbon-containing pyrolysis effluents. They are carried along by the inert gas stream whose flow rate can range between 20 ml/min and 70 ml/min.

IR spectrophotometer 8 analyzes the CO, the $CO_2$.

IR or UV spectrophotometer 9 analyzes the $SO_2$.

A water trap 12 that can contain magnesium perchlorate $Mg(ClO_4)_2$ is arranged at the outlet of pyrolysis effluent oxidation oven 5.

A water trap 12' that can contain drierite is arranged between stream divider 10 and CO and $CO_2$ detector 8.

A water trap 12" that can contain magnesium perchlorate is arranged at the outlet of oxidation oven 1'.

The effluents from oxidation oven 1' are sent to (respectively CO, $CO_2$ and $SO_2$) detectors 8 and 9 through pipes 13 and 14.

OPERATION OF THE DEVICE

1. Pyrolysis Stage

The pyrolysis stage is described here with reference to FIG. 1, which diagrammatically shows the elements in connection with pyrolysis oven 1.

A sample of a geological sediment, or of a petroleum product, for example a crude oil, an oil fraction or a petroleum distillate, is placed in boat 3. Depending on the type of sample used, the mass necessary for analysis is as follows:

| | |
|---|---|
| Rocks | 20 to 100 mg |
| Kerogens and coals | 2 to 20 mg |
| Petroleums, oils, petroleum distillates | 2 to 10 mg. |

Boat 3 is fed into pyrolysis oven 1 by means of automated piston 4. An inert gas (nitrogen, helium, etc.) is fed into the oven at a flow rate ranging between 50 ml/min and 200 ml/min, by means of pipe 2. This gas, referred to as carrier gas, sweeps the oven and carries along the effluents that are generated during pyrolysis.

Oven 1 is heated to between 60° C. and 800° C., with a predetermined temperature rise programme. The temperature increase phase takes place at a constant rate, generally ranging between 1° C./min and 50° C./min. The effluents generated are continuously swept by the carrier gas and carried out of the oven to gas stream divider 10.

The effluents are divided into three parts whose flow rate is adjusted and controlled by electronic devices:

towards FID detector 7, where the hydrocarbon compounds are measured, towards infrared spectrophotometer 8, where the CO and the $CO_2$ are measured, towards pyrolysis effluent oxidation oven 5. Prior to reaching this oven, the gas is mixed with a stream of air or oxygen delivered through pipe 11. This gas mixture enters oxidation oven 5 that is heated to a constant temperature ranging between 500° C. and 1000° C. Depending on the temperature selected, this oven can contain an oxidation catalyst such as tungsten trioxide. The sulfur compounds contained in the gas are predominantly converted to $SO_2$.

The gases then pass through a water trap 12 consisting of magnesium perchlorate $Mg(ClO_4)_2$ for example. The major part of the water contained in the gas is retained therein.

The gases reach detector 9 suited for continuous $SO_2$ measurement.

2. Oxidation Stage

The oxidation stage is described with reference to FIG. 1.

At the end of the pyrolysis stage, boat 3 is transferred by an automaton (not shown) from pyrolysis oven 1 to oxidation oven 1'.

Oxidation oven 1' is heated according to a temperature rise programme, from 100° C. to a final temperature that can reach 1300° C. This final temperature is adjusted according to the type of sample to be studied (oil, rock, etc.). The temperature increase phase takes place at a constant rate, generally ranging between 1° C./min and 50° C./min. During heating, air or oxygen is allowed into oven 1' by means of pipe 2', with a flow rate ranging between 50 ml/min and 200 ml/min. This gas, referred to as carrier gas, sweeps the oven and continuously carries along the effluents generated by oxidation.

During this stage, the sulfur remaining after pyrolysis is oxidized to $SO_2$. Similarly, the carbon remaining after pyrolysis is oxidized to CO and $CO_2$.

The effluents are sent out of the oven and percolate through water trap 12" where the major part of the water contained in the gas is retained. The $SO_2$, the CO and the $CO_2$ are continuously measured as a function of time with the detector specific to each species: spectrometer 8 for CO and $CO_2$, and spectrometer 9 for $SO_2$.

Calibration of the system is necessary to obtain a quantitative result.

APPLICATION EXAMPLES

Two application examples allowing to better understand the type of information on sulfur that is provided by the invention are described here. One example relates to a heavy crude oil and the other relates to a typical mother rock containing pyrite and sulfates.

FIG. 2a shows the $SO_2$ signal recorded during pyrolysis and FIG. 2b shows the $SO_2$ signal recorded during oxidation of a typical heavy crude oil sample. The abscissa axis represents time in seconds. The ordinate axis on the left represents the temperature in the oven. The ordinate axis on the right represents the $SO_2$ amount in milligrams measured per second. During pyrolysis, the oil is subjected to a temperature of 300° C. for 5 minutes, then to a temperature that increases at a rate of 25° C./min up to approximately 650° C. (dotted curve). Then, during oxidation (FIG. 2b), the pyrolysis residue is subjected to a constant temperature of 300° C. for 1 minute, then to a temperature increasing from 300° C. to 750° C. at a rate of 25° C./min (dotted curve).

In FIG. 2a, two peaks can be observed:

peak A, obtained from very labile organic sulfur compounds contained in the crude, peak B, obtained from labile organic sulfur compounds contained in the crude.

In FIG. 2b, peak C corresponds to the $SO_2$ from refractory organic sulfur compounds.

FIGS. 3a and 3b show the typical $SO_2$ signals that can be obtained with the invention on a mother rock containing sulfur in different forms: organic sulfur, contained in kerogen and in oil, pyrite sulfur and sulfate sulfur. During pyrolysis (FIG. 3a), the mother rock is subjected to a temperature of 300° C. for 5 minutes, then to a temperature increasing at a rate of 25° C./min up to approximately 650° C. (dotted curve). During oxidation (FIG. 3b), the pyrolysis residue is subjected to a constant temperature of 300° C. for 1 minute, then to a temperature increasing from 300° C. to 1200° C. at a rate of 25° C./min (dotted curve).

FIG. 3a shows three peaks:
peak A, obtained from very labile organic sulfur compounds,
peak B, obtained from labile organic sulfur compounds,
peak C, obtained from pyrite.

FIG. 3b shows three peaks:
peak D, obtained from refractory organic sulfur compounds,
peak E, obtained from pyrite,
peak F, obtained from sulfates.

Comparison of the Sulfur Content Measurements Performed by Means of the Present Invention and by Coulometry:

The sulfur content was measured on various types of samples, on the one hand with the present invention and on the other hand by coulometry. Coulometry is frequently used for quantifying the sulfur in rocks and in oils. It provides a reference measurement here.

The results presented in FIG. 4 were obtained on various samples such as oils containing between 0.5 wt. % and 5 wt % sulfur, kerogens containing between 10 wt. % and 20 wt. % sulfur, and sulfur polymers containing between 15 wt. % and 30 wt. % sulfur.

The abscissa axis represents the sulfur mass content measured by coulometry. The ordinate axis represents the sulfur mass content measured with the present invention. The results show a very good match between the two techniques, over a sulfur content range from 0.5 wt. % to 30 wt. %.

The invention claimed is:

1. A method for sulfur characterization and quantification in a sample of sedimentary rocks or of petroleum products, wherein the following stages are carried out:
heating said sample in a pyrolysis oven in a non-oxidizing atmosphere to a temperature resulting in release of pyrolysis effluents and production of pyrolysis residues,
transferring the pyrolysis residues produced from said sample into an oxidation oven, heating the pyrolysis residues in said oxidation oven according to a temperature resulting in release of effluents from said pyrolysis residues, and continuously measuring the amount of $SO_2$ contained in the effluents released from said heating in the oxidation oven,
oxidizing part of the pyrolysis effluents released from heating said sample in the pyrolysis oven and continuously measuring the amount of $SO_2$ contained in said part after oxidation.

2. A method as claimed in claim 1, further comprising:
measuring the amounts of hydrocarbon-containing products, of CO and of $CO_2$ contained in the pyrolysis effluents,
measuring the amounts of CO and of $CO_2$ contained in the effluents released from heating the pyrolysis residues in said oxidation oven.

3. A method as claimed in claim 1, wherein the temperature of the pyrolysis oven ranges between 60° C. and 800° C.

4. A method as claimed in claim 3, wherein the heating of the pyrolysis oven to the temperature resulting in release of pyrolysis effluents from said sample and production of pyrolysis residues from said sample comprises heating the pyrolysis oven at a rate between 1° C./min and 50° C./min.

5. A method as claimed in claim 1, wherein the temperature of the oxidation oven ranges between 100° C. and 1300° C.

6. A method as claimed in claim 5, wherein the heating of the oxidation oven to the temperature resulting in release of effluents from said pyrolysis residues comprises heating the oxidation oven at a rate between 1° C./min and 50° C./min.

7. A method as claimed in claim 1, wherein said part of the pyrolysis effluents is oxidized in an oven comprising a catalyst.

8. A device for sulfur characterization and quantification in a sample of sedimentary rocks or of petroleum products, comprising:
a pyrolysis oven configured to heat said sample in a non-oxidizing atmosphere as to induce the release of pyrolysis effluents from said sample and induce the production of pyrolysis residues from said sample,
an oxidation oven configured to heat the pyrolysis residues produced from said sample as to induce the release of effluents from said pyrolysis residues,
means for transferring the pyrolysis residues produced from said sample into said oxidation oven,
means for continuous measurement of the amount of $SO_2$ contained in the effluents released from said pyrolysis residues,
means for oxidizing part of the pyrolysis effluents released from said sample, and
means for continuous measurement of the amount of $SO_2$ contained in the effluents released from said sample after said oxidation.

9. A device as claimed in claim 8, further comprising:
means for continuous measurement of the amount of hydrocarbons contained in the pyrolysis effluents released from said sample,
means for continuous measurement of the amount of CO and $CO_2$ contained in the pyrolysis effluents released from said sample, and
three-way distribution means for the pyrolysis effluents, such that:
a first way carries a first portion of the pyrolysis effluents released from said sample from said pyrolysis oven to said oxidation means,
a second way carries a second portion of the pyrolysis effluents released from said sample from said pyrolysis oven to said means for continuous measurement of the amount of CO and $CO_2$ and
a third way carries a third portion of the pyrolysis effluents released from said sample form said pyrolysis to said means for continuous measurement of the amount of hydrocarbons.

10. A device as claimed in claim 9, wherein said distribution means are heated to a temperature ranging between 400° C. and 600° C.

11. A device as claimed in claim 8, wherein the means for oxidizing part of the pyrolysis effluents comprise an oven, a catalyst and an air supply means.

12. A device as claimed in claim 8, wherein the pyrolysis oven is further configured to:
heat the sample between 60° C. and 800° C., and
increase temperature with a heating rate ranging between 1° C./min and 50° C./min.

13. A device as claimed in claim 8, wherein the oxidation oven is further configured to:
heat the pyrolysis residues produced from said sample between 100° C. and 1300° C., and
increase temperature with a heating rate ranging between 1° C./min and 50° C./min.

14. A device for sulfur characterization and quantification in a sample of sedimentary rocks or of petroleum products, comprising:
a pyrolysis oven configured to heat said sample in a non-oxidizing atmosphere as to induce the release of pyrolysis effluents from said sample and induce the production of pyrolysis residues from said sample, a pyrolysis residue oxidation oven configured to heat the pyrolysis residues produced from said sample as to induce the release of effluents from said pyrolysis residues, a $SO_2$ detector continuously measuring the amount of $SO_2$ contained in the effluents released from said pyrolysis residues, an effluent oxidizing oven receiving at least a portion of the pyrolysis effluents released from said sample, the effluent oxidizing oven configured to oxidize the received pyrolysis effluents, and a $SO_2$ detector continuously measuring the amount of $SO_2$ contained in the effluents released from said sample and oxidized in the effluent oxidizing oven.

15. A device as claimed in claim 14, further comprising:

a carbon oxide detector continuously measuring the amount of CO and $CO_2$ contained in a second portion of the pyrolysis effluents released from said sample, a hydrocarbon detector continuously measuring the amount of hydrocarbons contained in a third portion of the pyrolysis effluents released from said sample, and a gas stream divider connecting the effluent oxidizing oven to the pyrolysis oven, connecting the carbon oxide detector to the pyrolysis oven, and connecting the hydrocarbon detector to the pyrolysis oven.

16. A device as claimed in claim 15, wherein said gas stream divider is heated to a temperature ranging between 400° C. and 600° C.

17. A device as claimed in claim 14, wherein the pyrolysis oven is further configured to:

heat the sample between 60° C. and 800° C., and increase temperature with a heating rate ranging between 1° C./min and 50° C./min.

18. A device as claimed in claim 14, wherein the pyrolysis residue oxidation oven is further configured to:

heat the pyrolysis residues produced from said sample between 100° C. and 1300° C., and increase temperature with a heating rate ranging between 1° C./min and 50° C./min.

19. A device as claimed in claim 14, wherein the effluent oxidizing oven comprises an oxidation catalyst.

20. A device as claimed in claim 14, further comprising an air supply configured to supply oxygen to the effluent oxidizing oven.

* * * * *